United States Patent [19]

Keil et al.

[11] Patent Number: 4,692,553
[45] Date of Patent: Sep. 8, 1987

[54] CYCLOHEXENONE DERIVATIVES AND THEIR USE FOR CONTROLLING UNDESIRABLE PLANT GROWTH

[75] Inventors: Michael Keil, Freinsheim; Ulrich Schirmer, Heidelberg; Dieter Jahn, Edingen-Neckarhausen; Rainer Becker, Bad Durkheim; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 759,257

[22] Filed: Jul. 26, 1985

[30] Foreign Application Priority Data

Jul. 27, 1984 [DE] Fed. Rep. of Germany ....... 3427695
Sep. 14, 1984 [DE] Fed. Rep. of Germany ....... 3433767

[51] Int. Cl.$^4$ .................. C07C 131/10; C07C 131/04; A01N 37/22; A01N 37/24
[52] U.S. Cl. .................................. 564/185; 558/426; 558/199; 558/241; 560/21; 560/27; 560/35; 560/313; 560/314; 560/251; 564/49; 564/50; 564/79; 564/95; 564/97; 564/99; 564/123; 564/162; 564/166; 564/179; 564/184; 564/189; 564/190; 564/202; 564/211; 564/212; 564/213; 564/220; 564/221; 564/256
[58] Field of Search ............... 564/185, 186, 184, 166; 71/118

[56] References Cited

FOREIGN PATENT DOCUMENTS 85529   8/1983  European Pat. Off. .
133349  2/1985  European Pat. Off. .
136703  4/1985  European Pat. Off. .
63052   1/1979  Japan .
1461170 7/1974  United Kingdom .
2116555 9/1983  United Kingdom .

OTHER PUBLICATIONS

Article: Houben–Weyl, "Methoden der Organischer-Chemie", p. 132, 4th Ed., (1952).

Primary Examiner—Charles F. Warren
Assistant Examiner—Carolyn S. Greason
Attorney, Agent, or Firm—Keil & Weinkauf

[57] ABSTRACT

Cyclohexenone derivatives of the formula

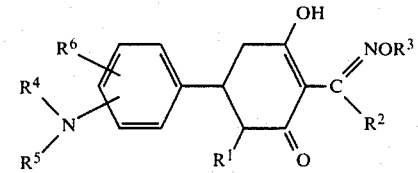

where $R^1$ is hydrogen, methoxycarbonyl, ethoxycarbonyl, methyl or cyano, $R^2$ is alkyl, $R^3$ is alkyl, alkenyl, haloalkenyl, or propargyl, $R^4$ is hydrogen or alkyl, $R^5$ is hydrogen, alkyl, acyl, formyl, cycloalkylcarbonyl, methoxyalkylcarbonyl, unsubstituted or substituted benzoyl, alkoxycarbonyl, benzyloxycarbonyl, phenoxycarbonyl, alkylthiocarbonyl, N,N-dialkylcarbamyl, N-alkylcarbamyl, N-cycloalkylcarbamyl, N-alkoxy-N-alkylcarbamyl, unsubstituted or substituted N-phenylcarbamyl, alkylsulfonyl, alkenylsulfonyl, haloalkylsulfonyl, N-alkylsulfamyl, N,N-dialkylsulfamyl, N-acyl-N-alkylsulfamyl, N-alkyl-N-methoxycarbonylsulfamyl, dialkoxyphosphoryl, dialkoxythiophosphoryl, 2-haloalkanoyl, acyloxyacetyl or alkoxyoxalyl, and $R^6$ is alkyl, halogen, hydroxyl, alkoxy, alkenyloxy, alkynyloxy, alkylthio, alkylsulfinyl, alkylsulfonyl, nitro or amino, and salts of these compounds, and the use of these compounds for controlling unwanted plant growth.

3 Claims, No Drawings

CYCLOHEXENONE DERIVATIVES AND THEIR USE FOR CONTROLLING UNDESIRABLE PLANT GROWTH

The present invention relates to cyclohexenone derivatives, herbicides which contain these compounds as active ingredients, and a method of controlling undesirable plant growth.

It has been disclosed that cyclohexenone derivatives can be used for controlling undesirable grasses in broad-leaved crops (DE-A No. 2 439 104). Furthermore, DE-A No. 3 248 554 discloses that cyclohexen-1-one derivatives which carry a para-substituted phenyl ring in the 5-position control gramineous weeds in corn and wheat.

We have found that cyclohexenone derivatives of the formula I

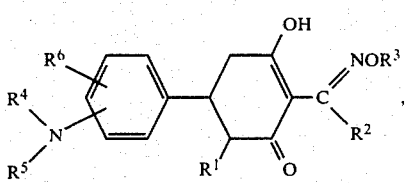

where $R^1$ is hydrogen, methoxycarbonyl, ethoxycarbonyl, methyl or cyano, $R^2$ is alkyl of 1 to 4 carbon atoms, $R^3$ is alkyl of 1 to 4 carbon atoms, alkenyl of 3 or 4 carbon atoms, haloalkenyl of 3 or 4 carbon atoms which possesses 1 to 3 halogen substituents, or propargyl, $R^4$ is hydrogen or alkyl of 1 to 4 carbon atoms, $R^5$ is hydrogen, alkyl, aliphatic acyl of 2 to 8 carbon atoms, formyl, cycloalkylcarbonyl of 4 to 7 carbon atoms, methoxyalkylcarbonyl, or benzoyl which is unsubstituted or substituted by nitro, halogen, alkyl or alkoxy, or is alkoxycarbonyl, benzyloxycarbonyl, phenoxycarbonyl, alkylthiocarbonyl, N,N-dialkylcarbamyl, N-alkylcarbamyl, N-cycloalkylcarbamyl where cycloalkyl is of 5 to 8 carbon atoms, N-alkoxy-N-alkylcarbamyl, N-phenylcarbamyl which is unsubstituted or substituted by nitro, halogen, alkyl, alkoxy or haloalkyl, or is alkylsulfonyl, alkenylsulfonyl, haloalkylsulfonyl, N-alkylsulfamyl, N,N-dialkylsulfamyl, N-acyl-N-alkylsulfamyl where acyl is of 2 to 5 carbon atoms, N-alkyl-N-methoxycarbonylsulfamyl, dialkoxyphosphoryl, dialkoxythiophosphoryl, 2-haloalkanoyl, acyloxyacetyl or alkoxyoxalyl, and $R^6$ is alkyl, halogen, hydroxyl, alkoxy, alkenyloxy, alkynyloxy, alkylthio, alkylsulfinyl, alkylsulfonyl, nitro or amino, and salts of these compounds possess a good herbicidal action, preferably against species from the grass family (gramineae). 3 or 4 carbon atoms which may contain not more than 3 halogen substituents, preferably chloroalkenyl, eg. methyl, ethyl, n-propyl, isopropyl, n-butyl, sec.-butyl, isobutyl, tert.-butyl, allyl, 1-chloroprop-1-en-3-yl, 2-chloroprop-1-en-3-yl, 1,3-dichloroprop-1-en-3-yl or 1,1,2-trichloroprop-1-en-3-yl, $R^4$ is hydrogen or alkyl of 1 to 4 carbon atoms, ie. methyl, ethyl, propyl, isopropyl, n-butyl, sec.-butyl, isobutyl, tert.-butyl, preferably hydrogen, $R^5$ is hydrogen, alkyl, aliphatic acyl of 2 to 8 carbon atoms, formyl, cycloalkylcarbonyl of 4 to 7 carbon atoms, methoxyalkylcarbonyl of 3 to 7 carbon atoms, benzoyl which is unsubstituted or substituted by nitro, halogen, alkyl or alkoxy, alkoxycarbonyl, benzyloxycarbonyl, phenoxycarbonyl, alkylthiocarbonyl, N,N-dialkylcarbamyl, N-alkylcarbamyl, N-cycloalkylcarbamyl where cycloalkyl is of 5 to 8 carbon atoms, N-alkoxy-N-alkylcarbamyl, or N-phenylcarbamyl which is unsubstituted or substituted by nitro, halogen, alkyl, alkoxy or haloalkyl, or is alkylsulfonyl, alkenylsulfonyl of 2 to 4 carbon atoms, haloalkylsulfonyl, haloalkenylsulfonyl of 2 to 4 carbon atoms, N-alkylsulfamyl, N,N-dialkylsulfamyl, N-acyl-N-alkylsulfamyl where acyl is of 2 to 5 carbon atoms, N-alkyl-N-methoxycarbonylsulfamyl, dialkoxyphosphoryl, dialkoxythiophosphoryl, 2-haloalkanoyl of 2 to 5 carbon atoms, acyloxyacetyl, where acyl is of 2 to 4 carbon atoms, or alkoxyoxalyl, preferably hydrogen, aliphatic acyl of 2 to 8 carbon atoms, or benzoyl which is unsubstituted or substituted by nitro, halogen, alkyl or alkoxy, particularly preferably hydrogen, acetyl or benzoyl, and $R^6$ is in the ortho-, meta or para-position and is halogen, hydroxyl or alkyl, alkoxy, alkenyloxy, alkynyloxy, alkylthio, alkylsulfinyl, or alkylsulfonyl, each of which is of not more than 4 carbon atoms, or nitro or amino, preferably halogen in particular fluorine or chlorine.

The alkyl groups $R^5$ and $R^6$, and the alkyl and alkoxy groups in the radicals stated for $R^5$ and $R^6$, may be straight-chain or branched and, unless stated otherwise, are each of 1 to 4 carbon atoms, ie. suitable alkyl and alkoxy groups are methyl, ethyl, n-propyl, isopropyl, n-butyl, sec.-butyl, isobutyl, tert.-butyl, methoxy, ethoxy, n-propoxy, isopropoxy, n-butoxy, isobutoxy, sec.-butoxy and tert.-butoxy.

$R^5$ is, for example, hydrogen, methyl, ethyl, acetyl, propionyl, butyryl, valeryl, formyl, cyclopropylcarbonyl, cyclopentylcarbonyl, cyclohexylcarbonyl, methoxyacetyl, 2-methoxypropionyl, 3-methoxypropionyl, benzoyl, 3-nitrobenzoyl, 2-chlorobenzoyl, 4-methylbenzoyl, 4-methoxybenzoyl, methoxycarbonyl, ethoxycarbonyl, benzyloxycarbonyl, phenoxycarbonyl, methylthiocarbonyl, ethylthiocarbonyl, isopropylthiocarbonyl, N,N-dimethylcarbamyl, N-methylcarbamyl, N-cyclohexylcarbamyl, N-methoxy-N-methylcarbamyl, N-(4-nitrophenyl)-carbamyl, N-(2-chlorophenyl)carbamyl, N-(3-methylphenyl)-carbamyl, N-(3-methoxyphenyl)carbamyl, N-methylsulfamyl, N,N-dimethylsulfamyl, N,N-diethylsulfamyl, N-acetyl-N-methylsulfamyl, N-butyryl-N-ethylsulfamyl, N-methoxycarbonyl-N-methylsulfamyl, N-isopropyl-N-methoxycarbonylsulfamyl, methylsulfonyl, chloromethylsulfonyl, trifluoromethylsulfonyl, prop-2-en-ylsulfonyl, 2,3,3-trichloroprop-2-en-ylsulfonyl, diethoxyphosphoryl, diethoxythiophosphoryl, chloroacetyl, 2-bromopropionyl, acetoxyacetyl, ethoxyoxalyl.

$R^6$ is, for example, methyl, ethyl, n-propyl, n-butyl, isopropyl, sec.-butyl, isobutyl, tert.-butyl, fluorine, chlorine, bromine, iodine, hydroxyl, methoxy, ethoxy, n-propoxy, isopropoxy, n-butoxy, isobutoxy, secbutoxy, tert.-butoxy, allyloxy, prop-2-ynyloxy, methylthio, ethylthio, methylsulfinyl, ethylsulfinyl, methylsulfonyl, ethylsulfonyl, nitro or amino.

Suitable salts of the compounds of the formula I are agriculturally useful salts, for example the alkali metal salts, in particular the potassium and sodium salts, alkaline earth metal salts, in particular calcium, magnesium and barium salts, manganese salts, copper salts, zinc salts and iron salts and ammonium and phosphonium salts, eg. alkylammonium, dialkylammonium, trialkylammonium or tetraalkylammonium salts, benzyltrialkylammonium salts, triphenylphosphonium salts, trialkylsulfonium salts and trialkylsulfoxonium salts.

The herbicidal cyclohexenone derivatives of the formula I can be obtained by reacting a tricarbonyl compound of the formula II

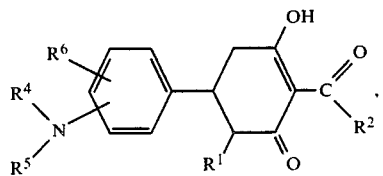

with an ammonium compound $R^3O—NH_3Y$, where $R^3$ has the above meanings and Y is an anion.

The reaction is advantageously carried out in the heterogeneous phase in an inert diluent at from 0° to 80° C. or from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. Organic bases, such as pyridine or tertiary amines, can also be used.

The reaction proceeds particularly well at a pH of from 2 to 9, in particular from 4.5 to 5.5. The pH is advantageously established by adding an acetate, for example an alkali metal acetate, in particular sodium or potassium acetate or a mixture of the two salts. Alkali metal acetates are added, for example, in amounts of from 0.5 to 2 moles per mole of the ammonium compound of the formula $R^3O—NH_3Y$.

Examples of suitable solvents are dimethyl sulfoxide, alcohols, such as methanol, ethanol or isopropanol, benzene, hydrocarbons or chlorohydrocarbons, such as chloroform, dichloroethane, hexane or cyclohexane, esters, such as ethyl acetate, and ethers, such as dioxane or tetrahydrofuran.

The reaction is complete after a few hours, and the product can be isolated by evaporating down the mixture, adding water and extracting with a non-polar solvent, such as methylene chloride, and distilling off the solvent under reduced pressure.

The compounds of the formula I may furthermore be obtained by reacting a tricarbonyl compound of the formula II with a hydroxylamine of the formula $R^3O—NH_2$, where $R^3$ has the above meanings, in an inert diluent at from 0° C. to the boiling point of the reaction mixture, in particular from 15° to 70° C. If necessary, the hydroxylamine can be used in the form of an aqueous solution.

Examples of suitable solvents for this reaction are alcohols, such as methanol, ethanol, isopropanol or cyclohexanol, hydrocarbons or chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

The alkali metal salts of the compounds of the formula I can be obtained by treating these compounds with sodium hydroxide or potassium hydroxide in aqueous solution or in an organic solvent, such as methanol, ethanol or acetone. Sodium alcoholates and potassium alcoholates may also serve as bases.

The other metal salts, eg. the manganese, copper, zinc, iron, calcium, magnesium and barium salts, can be prepared from the sodium salts by reaction with the corresponding metal chlorides in aqueous solution. Ammonium, phosphonium, sulfonium and sulfoxonium salts can be prepared by reacting a compound of the formula I with an ammonium, phosphonium, sulfonium or sulfoxonium hydroxide, if necessary in aqueous solution.

The novel tricarbonyl compounds of the formula II can be prepared from cyclohexane-1,3-diones of the formula

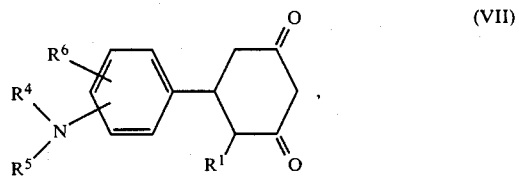

where $R^1$, $R^4$, $R^5$ and $R^6$ have the above meanings, by methods known from the literature (Tetrahedron Letters, 29, (1975), 2491).

It is also possible to obtain the novel compounds of the formula II via the enol-ester intermediates, which may be obtained as isomer mixtures in the acylation of compounds of the formula VII and undergo rearrangement in the presence of imidazole or pyridine derivatives (JP-A No.-63 052/1979).

As can be seen from the above statements, the novel tricarbonyl compounds of the formula II are useful intermediates for the preparation of the herbicidal compounds of the formula I.

The compounds of the formula VII are in turn obtained by methods known from the literature, as is evident from the scheme below:

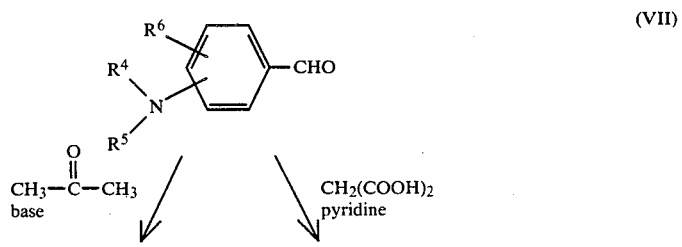

-continued

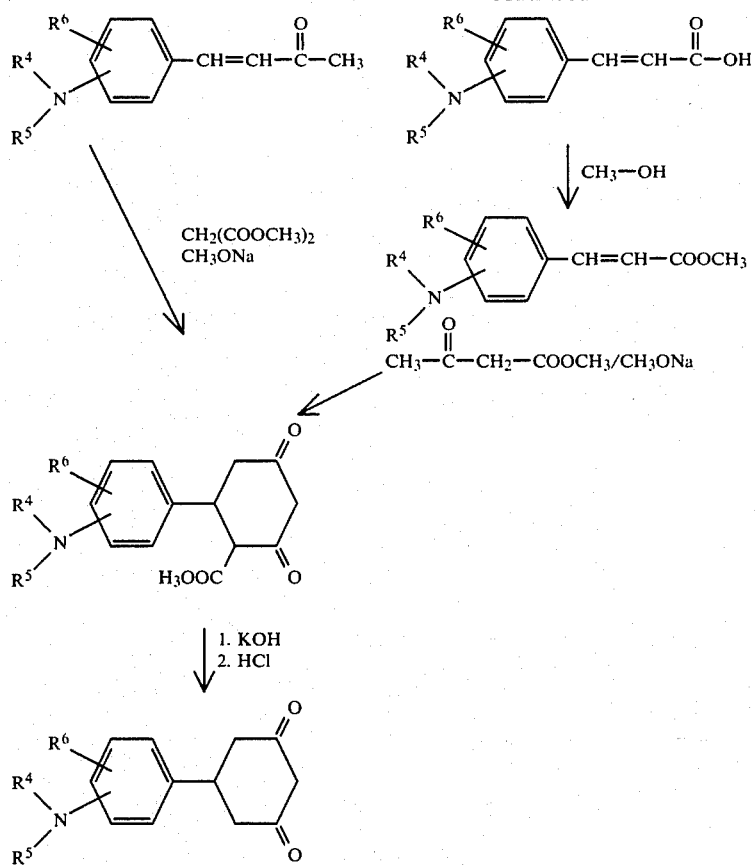

The cyclohexenone derivatives of the formula Ia

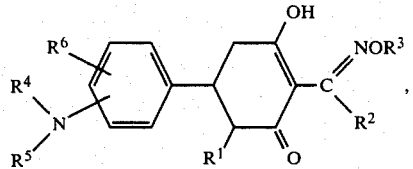

and the tricarbonyl compounds of the formula II

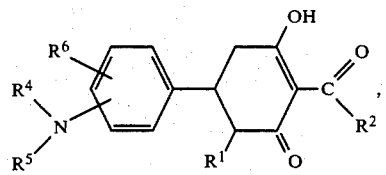

where $R^1$ and $R^4$ are each hydrogen, $R^2$ is alkyl of 1 to 4 carbon atoms, $R^3$ is alkyl of 1 to 4 carbon atoms, alkenyl of 3 or 4 carbon atoms, haloalkenyl of 3 or 4 carbon atoms which possesses 1 to 3 halogen substituents, or propargyl, $R^5$ is aliphatic acyl of 2 to 8 carbon atoms, formyl, cycloalkylcarbonyl of 4 to 7 carbon atoms, methoxyalkylcarbonyl, or benzoyl which is unsubstituted or substituted by nitro, halogen, alkyl or alkoxy, or is alkoxycarbonyl, benzyloxycarbonyl, phenoxycarbonyl, alkylthiocarbonyl, N,N-dialkylcarbamyl, N-alkoxy-N-alkylcarbamyl, alkylsulfonyl, alkenylsulfonyl, haloalkylsulfonyl, N-alkylsulfamyl, N,N-dialkylsulfamyl, N-acyl-N-alkylsulfamyl where acyl is of 2 to 5 carbon atoms, N-alkyl-N-methoxycarbonylsulfamyl, dialkoxyphosphoryl, dialkoxythiophosphoryl, 2-haloalkanoyl, acyloxyacetyl or alkoxyoxalyl, and $R^6$ is alkyl, halogen, hydroxyl, alkoxy, alkenyloxy, alkynyloxy, alkylthio, alkylsulfinyl, alkylsulfonyl, nitro or amino, can be obtained by reacting a compound of the formula Ia or II, where $R^5$ is hydrogen, with an electrophilic reagent of the formula $R^5Y_{(III)}$, where $R^5$ has the above meanings and Y is a leaving group, such as chlorine, bromine or carboxylate.

The reaction is, if necessary, carried out in an inert organic solvent, examples of suitable solvents being hydrocarbons, such as naphtha, gasoline, toluene, pentane, cyclohexane, halohydrocarbons, such as methylene chloride, chloroform, dichloroethane, chlorobenzene or o-, m- or p-dichlorobenzene, nitrohydrocarbons, such as nitrobenzene or nitromethane, nitriles, such as acetonitrile, butyronitrile or benzonitrile, ethers, such as diethyl ether, tetrahydrofuran or dioxane, esters, such as ethyl acetate or methyl propionate, ketones, such as acetone or methyl ethyl ketone, and amides, such as N,N-dimethylformamide or formamide, and mixtures of these solvents. The amount of solvent is from 100 to 5,000% by weight, based on aniline derivative employed.

Advantageously, the reaction is carried out in the presence of a conventional acid acceptor, suitable compounds being alkali metal hydroxides, alkali metal carbonates, alkali metal bicarbonates, alkaline earth metal hydroxides, alkaline earth metal carbonates, alkaline earth metal bicarbonates, alkaline earth metal oxides and amines, eg. sodium bicarbonate, potassium carbonate, triethylamine, tributylamine, pyridine, N,N-dimethylaniline, N,N-dimethyl-N-cyclohexylamine or quinoline. The amount of acid acceptor is from 1 to 4 moles per mole of aniline derivative employed.

The reaction temperature is from −20° to +150° C., preferably from 20° to 80° C. The electrophilic reagents $R^5Y$ and the compounds of the formula Ia and II which are used as starting compounds are preferably employed in equimolar amounts.

Examples of compounds of the formula $R^5Y$ are acyl halides, carboxylic anhydrides, chloroformates, alkylthiocarbonyl chlorides, N,N-dialkylcarbamyl chlorides, N-alkoxy-N-alkylcarbamyl chlorides, N-alkylsulfamyl chlorides and N-acyl-N-alkylsulfamyl chlorides, such as acyl halides of the formula

where $R^8$ is alkyl of 1 to 7 carbon atoms, cycloalkyl of 3 to 5 carbon atoms, methoxyalkyl of 2 to 4 carbon atoms or phenol which is unsubstituted or substituted by nitro, halogen, alkyl of 1 to 4 carbon atoms or alkoxy of 1 to 3 carbon atoms, formic acetic anhydride of the formula

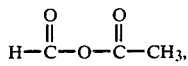

chloroformates of the formula

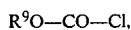

where $R^9$ is alkyl of 1 to 4 carbon atoms, benzyl or phenyl, alkylthiocarbonyl chlorides of the formula

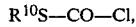

N,N-dialkylaminocarbamyl chlorides of the formula where $R^{10}$ is alkyl of 1 to 4 carbon atoms,

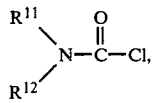

where $R^{11}$ and $R^{12}$ are each alkyl of 1 to 4 carbon atoms, N-alkoxy-N-alkylcarbamyl chlorides of the formula

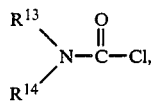

where $R^{13}$ is alkyl of 1 to 4 carbon atoms and $R^{14}$ is alkoxy of 1 to 4 carbon atoms, sulfonyl chlorides of the formula

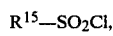

where $R^{15}$ is alkyl of 1 to 4 carbon atoms, alkenylsulfonyl of 3 or 4 carbon atoms, or haloalkylsulfonyl of not more than 3 halogen atoms, sulfamyl chlorides of the formula

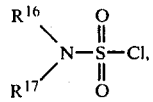

where $R^{16}$ is alkyl of 1 to 4 carbon atoms and $R^{17}$ is hydrogen, alkyl of 1 to 4 carbon atoms, acyl of 2 to 5 carbon atoms or methoxycarbonyl, dialkoxyphosphoryl or dialkoxythiophosphoryl chlorides of the formula

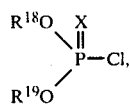

where X is O or S, and $R^{18}$ and $R^{19}$ are each alkyl of 1 to 4 carbon atoms, 2-haloalkanoyl chlorides of the formula

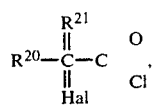

where $R^{20}$ and $R^{21}$ are each H or alkyl of 1 to 4 carbon atoms and Hal is fluorine, chlorine, bromine or iodine, acyloxyacetyl chlorides of the formula

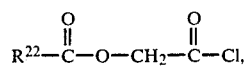

where $R^{22}$ is alkyl of 1 to 4 carbon atoms, and alkoxyoxalyl chlorides of the formula

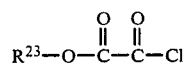

where $R^{23}$ is alkyl of 1 to 4 carbon atoms.

Furthermore, the cyclohexenone derivatives of the formula Ic

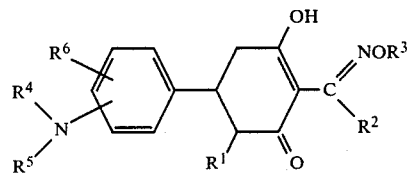

and the tricarbonyl compounds of the formula II

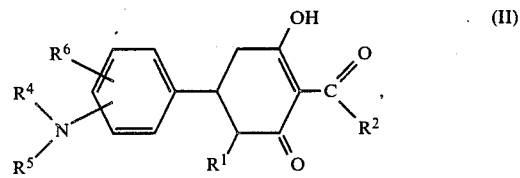

where $R^1$ and $R^4$ are each hydrogen, $R^2$ is alkyl of 1 to 4 carbon atoms, $R^5$ is N-alkylcarbamyl, N-cycloalkylcarbamyl, where cycloalkyl is of 5 to 8 carbon atoms, or N-phenylcarbamyl which is unsubstituted or substituted by nitro, halogen, alkyl or alkoxy, and $R^6$ is alkyl, halogen, hydroxyl, alkoxy, alkenyloxy, alkynyloxy, alkylthio, alkylsulfinyl, alkylsulfonyl, nitro or amino, are obtained by reacting the corresponding amino derivative with an isocyanate of the formula $$R^7-NCO \qquad (IV)$$

where $R^7$ is a radical which leads to appropriate radicals $R^5$ in formulae I and II when the reaction is complete.

The reaction is carried out in the presence or absence of a catalyst conventionally used for isocyanate reactions, for example a tertiary amine, such as triethylamine or 1,4-diazabicyclo[2.2.2]octane, nitrogen-containing heterocycles, such as pyridine or 1,2-dimethylimidazole, or organo-tin compounds, such as dibutyl-tin diacetate or dimethyl-tin dichloride, and in the presence or absence of a solvent which is inert under the reaction conditions, for example a hydrocarbon, such as naphtha, gasoline, toluene, pentane or cyclohexane, a halohydrocarbon, such as methyl chloride, chloroform, dichloroethane, chlorobenzene or o-, m- or p-dichlorobenzene, a nitrohydrocarbon, such as nitrobenzene or nitromethane, a nitrile, such as acetonitrile, butyronitrile or benzonitrile, in ether, such as diethyl ether, tetrahydrofuran or dioxane, an ester, such as ethyl acetate or methyl propionate, a ketone, such as acetone or methyl ethyl ketone, or an amide, such as N,N-dimethylformamide or formamide (Houben-Weyl, Methoden der organischen Chemie, vol. VIII, page 132, Georg Thieme-Verlag, Stuttgart, 4th edition, 1952).

The amount of catalyst is from 0.1 to 5 mol %, based on the aniline derivative employed. The amount of solvent varies from 100 to 10,000% by weight. The reaction temperature can vary from $-20°$ to $+150°$ C., preferably from 0° to 100° C.

The catalytic hydrogenation of nitro compounds of the formula V gives the corresponding amino compounds of the formula Ib:

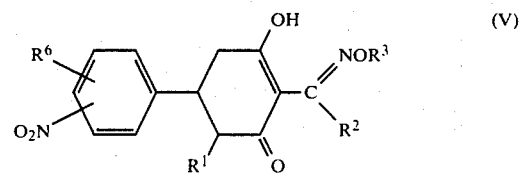

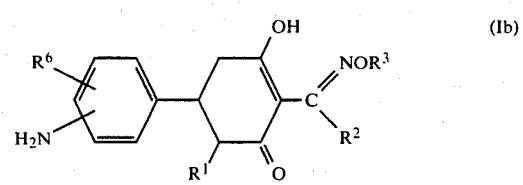

This reaction is carried out in the presence or absence of an inert solvent, eg. tetrahydrofuran, dioxane, a $C_1$–$C_4$-alcohol, ethylene glycol monomethyl ether, ethylene glycol monoethyl ether, N,N-dimethylformamide, pyridine, ethyl acetate, acetone, water or a mixture of these, under from 1 to 5 bar, preferably under atmospheric pressure, with the addition of a conventional hydrogenation catalyst, such as palladium, platinum or nickel, at from 0° to 80° C., preferably at room temperature.

The derivatives of the formula VI which are required for the preparation of the compounds V can be obtained by various methods:

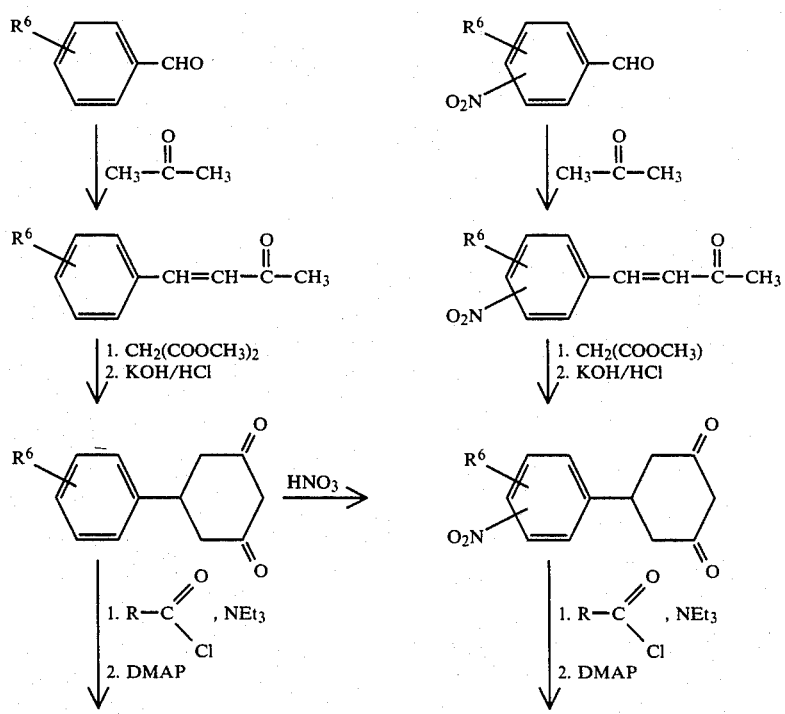

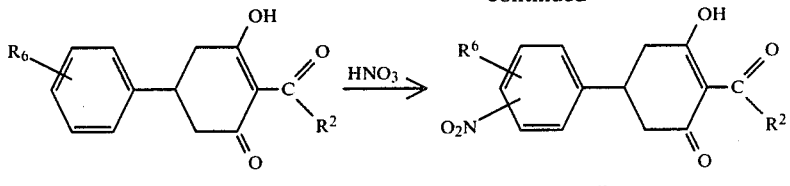

(VI)

The position at which the nitro group is introduced into the dicarbonyl or tricarbonyl intermediate depends critically on $R^6$, in accordance with the rules of electrophilic aromatic substitution, for example:

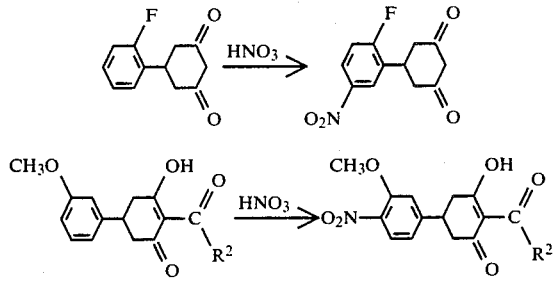

The Examples which follow illustrate the preparation of the cyclohexenone derivatives of the formula I.

EXAMPLE 1

5.3 g of 2-butyryl-5-(3-nitro-4-methoxyphenyl)cyclohexane-1,3-dione in 300 ml of tetrahydrofuran were hydrogenated in the presence of 3 g of Pd/carbon (10%) under atmospheric pressure at 25° C. After 0.9 l of hydrogen had been absorbed, the mixture was dried over sodium sulfate and filtered, 1.3 g of sodium bicarbonate were added and the mixture was reacted with 1.2 g of acetyl chloride. After the mixture had been stirred for 16 hours, it was filtered and evaporated down. The remaining oil was brought to crystallization with diethyl ether, and the crystals were filtered off under suction. 3 g (55% yield) of 5-(3-acetylamino-4-methoxyphenyl)-2-butyryl-3-hydroxycyclohex-2-en-1-one of melting point 102°–106° C. were obtained.

EXAMPLE 2

3 g of 5-(3-acetylamino-4-methoxyphenyl)-2-butyryl-3-hydroxycyclohex-2-en-1-one were stirred together with 0.95 g of O-allylhydroxylamine hydrochloride and 0.8 g of sodium bicarbonate in 40 ml of methanol for 16 hours. The mixture was evaporated down, mixed with methylene chloride, washed thoroughly with water, dried and evaporated down again. The residue which remained was stirred with diisopropyl ether and the product was filtered off under suction. 2.0 g (57% yield) of 5-(3-acetylamino-4-methoxyphenyl)-2-(1-allyloxyiminobutyl)-3-hydroxycyclohex-2-en-1-one of melting point 136°–137° C. were obtained (compound No. 11).

EXAMPLE 3

1.3 g of methanesulfonyl chloride were added to 4 g of 2-(1-ethoxyiminobutyl)-3-hydroxy-5-(3-amino-4-methoxyphenyl)-cyclohex-2-en-1-one in 50 ml of pyridine at 25° C., and the reaction solution was stirred for 16 hours, poured onto ice and brought to pH 1 with hydrochloric acid. The mixture was extracted with methylene chloride, and the organic phase was dried and evaporated down to give 3.6 g (74% yield) of 2-(1-ethoxyiminobutyl)-3-hydroxy-5-(4-methoxy-3-methoxysulfonamidophenyl)-cyclohex-2-en-1-one of melting point 108°–116° C. (decomposition) (compound No. 64).

EXAMPLE 4

4 g of 5-(3-amino-4-methoxyphenyl)-2-(1-ethoxyiminobutyl)-3-hydroxycyclohex-2-en-1-one in 50 ml of pyridine were stirred with 2.2 g of diethoxythiophosphoryl chloride for 16 hours at 25° C., and the reaction solution was poured onto ice and brought to pH 1 with hydrochloric acid. The mixture was extracted with methylene chloride, and the solution was filtered over silica gel and evaporated down to give 4 g (69% yield) of an oil consisting of 5-(3-diethoxythiophosphorylamido-4-methoxyphenyl)-2-(1-ethoximinobutyl)-3-hydroxycyclohex-2-en-1-one (compound No. 76).

EXAMPLE 5

4 g of 5-(3-amino-4-methoxyphenyl)-2-(1-ethoxyiminobutyl)-3-hydroxycyclohex-2-en-1-one in 50 ml of pyridine were stirred with 1.5 g of methylaminosulfonyl chloride for 16 hours at 25° C., and the reaction solution was poured onto ice and brought to pH 1 with hydrochloric acid. The mixture was extracted with methylene chloride and the organic phase was dried and evaporated down to give 2.2 g (43% yield) of 2-(1-ethoxyiminobutyl)-3-hydroxy-5-(4-methoxy-3-N-methyl-sulfamylamido)-cyclohex-2-en-1-one of melting point 56°–58° C. (compound No. 75).

EXAMPLE 6

31 g of 2-acetyl-3-hydroxy-5-(2-methoxyphenyl)cyclohex-2-en-1-one were dissolved in 140 ml of glacial acetic acid, 140 ml of concentrated sulfuric acid were added to the cooled solution at 25° C., 7.7 g of 98% strength nitric acid were rapidly added dropwise, the mixture was stirred for 30 minutes and then poured into an ice/methylene chloride mixture, and the organic phase was separated off, washed with water and dried over sodium sulfate. The dark oil obtained when the solution was evaporated down was dissolved in methylene chloride and then filtered over silica gel, and the solution was evaporated down to give 27.5 g (76% yield) of yellowish crystals consisting of 20% of 2-acetyl-3-hydroxy-5-(2-methoxy-3-nitrophenyl)-cyclohex-2-en-1-one (A) and 80% of 2-acetyl-3-hydroxy-5-(2-methoxy-5-nitrophenyl)-cyclohex-2-en-1-one (B) and having a mixed melting point of 145°–151° C.

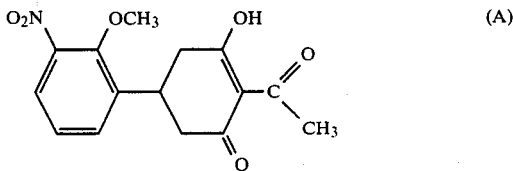

(A)

-continued

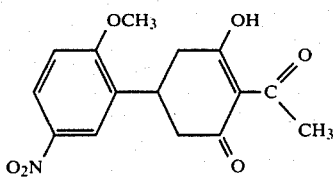
(B)

15 g of the above product mixture consisting of A and B in a ratio of 1:4 were stirred together with 4.2 g of sodium bicarbonate and 4.6 g of O-ethylhydroxylammonium chloride in methanol for 16 hours, the mixture was evaporated down, the residue was taken up in methylene chloride, the solution was extracted by shaking with water, dried and evaporated down. The residue was triturated in diisopropyl ether and the product was filtered off under suction. 15.5 g (91% yield) of the corresponding O-ethyloxime ethers C and D were obtained, once again in the form of a 1:4 mixture (mixed melting point 132°–142° C.).

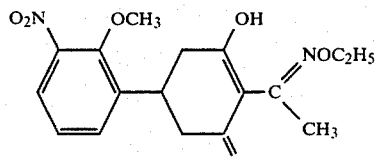
(C)

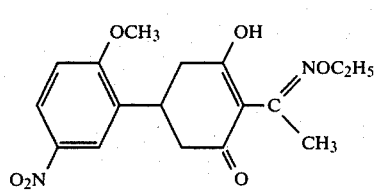
(D)

10.3 g of the 1:4 product mixture of C and D in 500 ml of tetrahydrofuran were hydrogenated in the presence of 3 g of palladium on carbon (10%) under atmospheric pressure at 25° C. After 3 l of hydrogen had been absorbed, the mixture was dried over sodium sulfate, filtered and evaporated down. 9.5 g of an oily 1:4 mixture of the corresponding anilines E and F were obtained, the yield being quantitative.

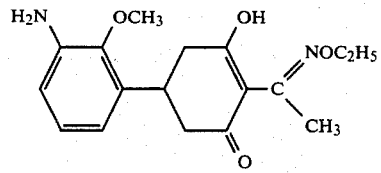
(E)

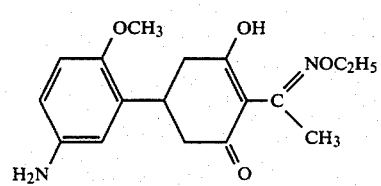
(F)

9 g of this aniline mixture were dissolved in 50 ml of tetrahydrofuran, 2.4 g of sodium bicarbonate were added and the stirred mixture was reacted with 2.2 g of acetyl chloride. Stirring was continued for 16 hours, after which the mixture was filtered, the filtrate was evaporated down and the oil which remained was chromatographed over silica gel using ethyl acetate. 0.9 g (9% yield) of the pure 5-(3-acetamido-2-methoxyphenyl)-2-(1-ethoximinoethyl)-3-hydroxycyclohex-2-en-1-one isomer,

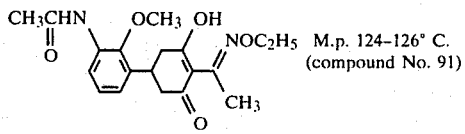
M.p. 124–126° C.
(compound No. 91)

and 3.6 g (35% yield) of the pure 5-(5-acetamido-2-methoxyphenyl)-2-(1-ethoxyiminoethyl)-3-hydroxycyclohex-2-en-1-one isomer,

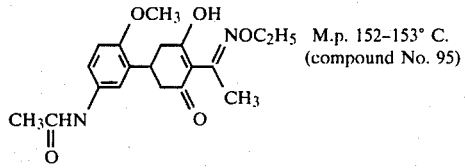
M.p. 152–153° C.
(compound No. 95)

were obtained.

EXAMPLE 7

60 g of 5-(2-fluorophenyl)-cyclohexane-1,3-dione were dissolved in 500 ml of concentrated sulfuric acid at −20° C. and nitrated with 18.3 g of 98% strength nitric acid at −20° C. in the course of 60 minutes. The reaction mixture was stirred into 5 l of ice water, and the precipitated crystals were filtered off under suction and dried. 60.5 g (83% yield) of 5-(2-fluoro-5-nitrophenyl)-cyclohexane-1,3-dione of melting point 171°–173° C. were obtained.

54 g of the above product were dissolved in 500 ml of methylene chloride, 18.7 g of pyridine were added and O-acylation was carried out at room temperature in the course of 1 hour using 25.2 g of butyryl chloride. The mixture was stirred for 16 hours, after which it was extracted by shaking with ice water, with 5% strength sodium bicarbonate solution and again with ice water, dried over sodium sulfate and evaporated down. The oil which remained was taken up in about 300 ml of ethyl acetate and left to stand together with 3 g of 4-dimethylaminopyridine for 5 days. The organic phase was extracted twice by shaking with 5% strength hydrochloric acid, dried and evaporated down. The residue which remained was recrystallized from isopropanol to give 33 g (48% yield) of 2-butyryl-5-(2-fluoro-5-nitrophenyl)-3-hydroxycyclohex-2-en-1-one of melting point 132° C.

25 g of the above product, 7.4 g of sodium bicarbonate and 8.6 g of O-ethylhydroxylammonium chloride in 100 ml of methanol were stirred for 16 hours, the mixture was evaporated down, the residue was taken up in methylene chloride, and the solution was washed with water, dried and evaporated down again. 24 g (84% yield) of 2-(1-ethoximinobutyl)-5-(2-fluoro-5-nitrophenyl)-3-hydroxycyclohex-2-en-1-one were obtained as a viscous oil.

23 g of this oil in 500 ml of tetrahydrofuran were hydrogenated in the presence of 5 g of palladium on carbon (10%) under atmospheric pressure at 25° C. After 4.5 l of hydrogen had been absorbed, the mixture was dried, filtered and evaporated down. 19.6 g (93% yield) of 5-(5-amino-2-fluorophenyl)-2-(1-ethoximinobutyl)-3-hydroxycyclohex-2-en-1-one were obtained as a viscous oil.

5.5 g of this product in 50 ml of tetrahydrofuran were left to stand together with 1 g of methyl isocyanate and 1 drop of dibutyl-tin diacetate for 4 days at room temperature. The mixture was evaporated down and the residue was stirred thoroughly with ether and dried. 4.4 g (69% yield) of 2-(1-ethoximinobutyl)-5-[2-fluoro-5-(3-methylureido)-phenyl]-3-hydroxycyclohex-2-en-1-one of melting point 120°–122° C. were obtained (compound No. 116).

The following cyclohexenone derivatives of the formula I were obtained in a similar manner:

| Compound No. | $R^5$ | $R^1$ | $R^2$ | $R^3$ | $R^4$ | M.p. [°C.] |
|---|---|---|---|---|---|---|
| 1 | H | H | $n$-$C_3H_7$ | $C_2H_5$ | H | 76–78 |
| 2 | H | H | $C_2H_5$ | $C_2H_5$ | H | |
| 3 | H | H | $C_2H_5$ | $CH_2$—$CH$=$CH_2$ | H | |
| 4 | H | H | $n$-$C_3H_7$ | $CH_2$—$CH$=$CH_2$ | H | |
| 5 | methyl | H | $n$-$C_3H_7$ | $C_2H_5$ | $CH_3$ | |
| 6 | methyl | H | $n$-$C_3H_7$ | $CH_2$—$CH$=$CH_2$ | $CH_3$ | |
| 7 | acetyl | H | $n$-$C_3H_7$ | $C_2H_5$ | H | 139–141 |
| 8 | acetyl | $COOCH_3$ | $C_2H_5$ | $C_2H_5$ | H | 54–61 |
| 9 | acetyl | H | $CH_3$ | $C_2H_5$ | H | 130–133 |
| 10 | acetyl | H | $C_2H_5$ | $C_2H_5$ | H | 124–126 |
| 11 | acetyl | H | $C_3H_7$ | $CH_2CH$=$CH_2$ | H | 136–137 |
| 12 | butyryl | H | $n$-$C_3H_7$ | $C_2H_5$ | H | |
| 13 | butyryl | H | $n$-$C_3H_7$ | $CH_2$—$CH$=$CH_2$ | H | |
| 14 | butyryl | H | $C_2H_5$ | $CH_2$—$CH$=$CH_2$ | H | |
| 15 | butyryl | H | $C_2H_5$ | $C_2H_5$ | H | |
| 16 | formyl | H | $n$-$C_3H_7$ | $C_2H_5$ | H | 117–118 |
| 17 | formyl | H | $n$-$C_3H_7$ | $CH_2$—$CH$=$CH_2$ | H | |
| 18 | formyl | H | $C_2H_5$ | $CH_2$—$CH$=$CH_2$ | H | |
| 19 | formyl | H | $C_2H_5$ | $C_2H_5$ | H | |
| 20 | formyl | H | $n$-$C_3H_7$ | $CH_2$—$CH$=$CHCl$ | H | |
| 21 | cyclopropylcarbonyl | H | $n$-$C_3H_7$ | $C_2H_5$ | H | 131–135 |
| 22 | cyclopropylcarbonyl | H | $n$-$C_3H_7$ | $CH_2$—$CH$=$CH_2$ | H | |
| 23 | cyclopropylcarbonyl | H | $C_2H_5$ | $CH_2$—$CH$=$CH_2$ | H | |
| 24 | cyclopropylcarbonyl | H | $C_2H_5$ | $C_2H_5$ | H | |
| 25 | methoxyacetyl | H | $n$-$C_3H_7$ | $C_2H_5$ | H | 138–140 |
| 26 | methoxyacetyl | H | $n$-$C_3H_7$ | $CH_2$—$CH$=$CH_2$ | H | |
| 27 | methoxyacetyl | H | $C_2H_5$ | $CH_2$—$CH$=$CH_2$ | H | |
| 28 | methoxyacetyl | H | $C_2H_5$ | $C_2H_5$ | H | 127–130 |
| 29 | 3-methoxypropionyl | H | $n$-$C_3H_7$ | $C_2H_5$ | H | 93–97 |
| 30 | 3-methoxypropionyl | H | $n$-$C_3H_7$ | $CH_2$—$CH$=$CH_2$ | H | |
| 31 | 3-methoxypropionyl | H | $C_2H_5$ | $CH_2$—$CH$=$CH_2$ | H | |
| 32 | 3-methoxypropionyl | H | $C_2H_5$ | $C_2H_5$ | H | |
| 33 | benzoyl | H | $n$-$C_3H_7$ | $C_2H_5$ | H | 110–112 |
| 34 | benzoyl | H | $n$-$C_3H_7$ | $CH_2$—$CH$=$CH_2$ | H | |
| 35 | benzoyl | H | $C_2H_5$ | $CH_2$—$CH$=$CH_2$ | H | |
| 36 | benzoyl | $COOCH_3$ | $C_2H_5$ | $C_2H_5$ | H | |
| 37 | 3-nitrobenzoyl | H | $n$-$C_3H_7$ | $C_2H_5$ | H | |
| 38 | 3-methoxybenzoyl | H | $n$-$C_3H_7$ | $C_2H_5$ | H | |
| 39 | 4-chlorobenzoyl | H | $C_2H_5$ | $C_2H_5$ | H | |
| 40 | methoxycarbonyl | H | $n$-$C_3H_7$ | $C_2H_5$ | H | 110–113 |
| 41 | methoxycarbonyl | H | $n$-$C_3H_7$ | $CH_2$—$CH$=$CH_2$ | H | |
| 42 | methoxycarbonyl | H | $C_2H_5$ | $CH_2$—$CH$=$CH_2$ | H | |
| 43 | methoxycarbonyl | H | $C_2H_5$ | $C_2H_5$ | H | 125–127 |
| 44 | methylthiocarbonyl | H | $n$-$C_3H_7$ | $C_2H_5$ | H | 106–108 |
| 45 | methylthiocarbonyl | H | $n$-$C_3H_7$ | $CH_2$—$CH$=$CH_2$ | H | |
| 46 | methylthiocarbonyl | H | $C_2H_5$ | $CH_2$—$CH$=$CH_2$ | H | |
| 47 | methylthiocarbonyl | H | $C_2H_5$ | $C_2H_5$ | H | 118–120 |
| 48 | chloroacetyl | H | $n$-$C_3H_7$ | $C_2H_5$ | H | 125–130 |
| 49 | 2-bromopropionyl | H | $n$-$C_3H_7$ | $C_2H_5$ | H | 139–142 |
| 50 | ethoxyoxalyl | H | $n$-$C_3H_7$ | $C_2H_5$ | H | 118–120 |
| 51 | acetoxyacetyl | H | $n$-$C_3H_7$ | $C_2H_5$ | H | 117–122 |
| 52 | N,N—dimethylcarbamoyl | H | $n$-$C_3H_7$ | $C_2H_5$ | H | |
| 53 | N,N—dimethylcarbamoyl | H | $n$-$C_3H_7$ | $CH_2$—$CH$=$CH_2$ | H | |
| 54 | N,N—dimethylcarbamoyl | H | $C_2H_5$ | $CH_2$—$CH$=$CH_2$ | H | |
| 55 | N,N—dimethylcarbamoyl | H | $C_2H_5$ | $C_2H_5$ | H | |
| 56 | N—methylcarbamoyl | H | $n$-$C_3H_7$ | $C_2H_5$ | H | 105–107 |
| 57 | N—methylcarbamoyl | H | $n$-$C_3H_7$ | $CH_2CH$=$CH_2$ | H | |
| 58 | N—methylcarbamoyl | H | $C_2H_5$ | $CH_2$—$CH$=$CH_2$ | H | |
| 59 | N—methylcarbamoyl | $COOCH_3$ | $C_2H_5$ | $C_2H_5$ | H | 80–82 |
| 60 | N—methoxy—N—methylcarbamoyl | H | $n$-$C_3H_7$ | $C_2H_5$ | H | 96–99 |
| 61 | N—methoxy—N—methylcarbamoyl | $COOCH_3$ | $C_2H_5$ | $C_2H_5$ | H | 85–107 |
| 62 | N—methoxy—N—methylcarbamoyl | H | $C_2H_5$ | $CH_2$—$CH$=$CH_2$ | H | |

-continued

| No. | | | | | | mp |
|---|---|---|---|---|---|---|
| 63 | N—methoxy—N—methylcarbamoyl | H | $C_2H_5$ | $C_2H_5$ | H | 91-93 |
| 64 | methylsulfonyl | H | n-$C_3H_7$ | $C_2H_5$ | H | 108-116 (decomp.) |
| 65 | methylsulfonyl | H | n-$C_3H_7$ | $CH_2-CH=CH_2$ | H | |
| 66 | methylsulfonyl | H | $C_2H_5$ | $CH_2-CH=CH_2$ | H | |
| 67 | methylsulfonyl | H | $C_2H_5$ | $C_2H_5$ | H | 168-170 |
| 68 | trifluoromethylsulfonyl | H | n-$C_3H_7$ | $C_2H_5$ | H | |
| 69 | trifluoromethylsulfonyl | H | n-$C_3H_7$ | $CH_2-CH=CH_2$ | H | |
| 70 | trifluoromethylsulfonyl | H | $C_2H_5$ | $CH_2-CH=CH_2$ | H | |
| 71 | trifluoromethylsulfonyl | H | $C_2H_5$ | $C_2H_5$ | H | |
| 72 | chloromethylsulfonyl | H | n-$C_3H_7$ | $C_2H_5$ | H | |
| 73 | chloromethylsulfonyl | H | n-$C_3H_7$ | $CH_2-CH=CH_2$ | H | |
| 74 | N-isobutylsulfamoyl | H | $C_2H_5$ | $C_2H_5$ | H | |
| 75 | N-methylsulfamoyl | H | n-$C_3H_7$ | $C_2H_5$ | H | 56-58 |
| 76 | diethoxythiophosphoryl | H | n-$C_3H_7$ | $C_2H_5$ | H | (NMR data) |
| 77 | diethoxyphosphoryl | H | n-$C_3H_7$ | $C_2H_5$ | H | (NMR data) |
| 136 | H | $COOCH_3$ | $C_2H_5$ | $C_2H_5$ | H | (NMR data) |
| 137 | H | H | $CH_3$ | $C_2H_5$ | H | 118-121 |
| 138 | methoxyacetyl | H | $CH_3$ | $C_2H_5$ | H | 120-124 |
| 139 | benzoyl | H | $C_2H_5$ | $C_2H_5$ | H | 120-121 |
| 140 | benzoyl | H | $CH_3$ | $C_2H_5$ | H | 134-139 |
| 141 | acetoxyacetyl | H | $C_2H_5$ | $C_2H_5$ | H | 103-105 |
| 142 | N—methylcarbamoyl | H | $C_2H_5$ | $C_2H_5$ | H | 143-146 |

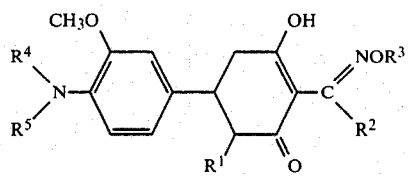

| 78 | H | H | n-$C_3H_7$ | $C_2H_5$ | H | oil |
|---|---|---|---|---|---|---|
| 79 | H | H | $C_2H_5$ | $C_2H_5$ | H | |
| 80 | N—methylcarbamoyl | H | n-$C_3H_7$ | $C_2H_5$ | $CH_3$ | |
| 81 | acetyl | H | n-$C_3H_7$ | $C_2H_5$ | H | |
| 82 | acetyl | H | n-$C_3H_7$ | $CH_2-CH=CH_2$ | H | |
| 143 | acetyl | H | n-$C_3H_7$ | n-$C_3H_7$ | H | 69-72 |
| 144 | benzoyl | H | n-$C_3H_7$ | $C_2H_5$ | H | 112-114 |
| 145 | methoxyacetyl | H | n-$C_3H_7$ | $C_2H_5$ | H | 95-99 |

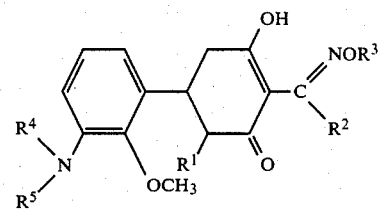

| 83 | H | H | n-$C_3H_7$ | $C_2H_5$ | H | |
|---|---|---|---|---|---|---|
| 84 | H | H | $C_2H_5$ | $C_2H_5$ | H | |
| 85 | H | H | $C_2H_5$ | $CH_2-CH=CH_2$ | H | |
| 86 | H | H | $CH_3$ | $C_2H_5$ | H | oil |
| 87 | H | H | $CH_3$ | $CH_2-CH=CH_2$ | H | |
| 88 | methyl | H | n-$C_3H_7$ | $C_2H_5$ | $CH_3$ | |
| 89 | methyl | H | n-$C_3H_7$ | $CH_2-CH=CH_2$ | $CH_3$ | |
| 90 | methyl | H | $C_2H_5$ | $CH_2-CH=CH_2$ | $CH_3$ | |
| 91 | acetyl | H | $CH_3$ | $C_2H_5$ | H | 124-126 |
| 146 | acetyl | H | $C_2H_5$ | $C_2H_5$ | H | |
| 147 | acetyl | H | $C_2H_5$ | $CH_2CH_2Cl$ | H | |
| 148 | acetyl | H | $C_2H_5$ | (E)-$CH_2-CH=CH-CH_3$ | H | |
| 149 | acetyl | H | $C_2H_5$ | (E)-$CH_2-CH=CH-CH_3$ | H | |
| 150 | acetyl | H | $C_2H_5$ | $CH_2-CH=CH_2$ | H | |
| 151 | acetyl | H | n-$C_3H_7$ | $C_2H_5$ | H | 96-98 |
| 152 | acetyl | H | n-$C_3H_7$ | $CH_2-CH_2Cl$ | H | |
| 153 | acetyl | H | n-$C_3H_7$ | $CH_2CH_2F$ | H | |
| 154 | acetyl | H | n-$C_3H_7$ | (E)-$CH_2-CH=CH-CH_3$ | H | |
| 155 | acetyl | H | n-$C_3H_7$ | (E)-$CH_2-CH=CH-Cl$ | H | |
| 156 | acetyl | H | n-$C_3H_7$ | $CH_2-CH=CH_2$ | H | |
| 157 | propionyl | H | $C_2H_5$ | $C_2H_5$ | H | |
| 158 | propionyl | H | $C_2H_5$ | $CH_2-CH=CH_2$ | H | |
| 159 | propionyl | H | n-$C_3H_7$ | $CH_2-CH=CH_2$ | H | |
| 160 | propionyl | H | n-$C_3H_7$ | $C_2H_5$ | H | |
| 161 | butyryl | H | $C_2H_5$ | $C_2H_5$ | H | |
| 162 | butyryl | H | $C_2H_5$ | $CH_2-CH=CH_2$ | H | |
| 163 | butyryl | H | n-$C_3H_7$ | $CH_2-CH=CH_2$ | H | |
| 164 | butyryl | H | n-$C_3H_7$ | $C_5H_5$ | H | |
| 165 | chloroacetyl | H | n-$C_3H_7$ | $C_2H_5$ | H | |
| 166 | chloroacetyl | H | n-$C_3H_7$ | $CH_2-CH=CH_2$ | H | |

-continued

| | | | | | | |
|---|---|---|---|---|---|---|
| 167 | chloroacetyl | H | C₂H₅ | CH₂—CH=CH₂ | H | |
| 168 | chloroacetyl | H | C₂H₅ | C₂H₅ | H | |
| 169 | methoxyacetyl | H | C₂H₅ | C₂H₅ | H | |
| 170 | methoxyacetyl | H | C₂H₅ | CH₂—CH=CH₂ | H | |
| 171 | methoxyacetyl | H | n-C₃H₇ | CH₂—CH=CH₂ | H | |
| 172 | methoxyacetyl | H | n-C₃H₇ | C₂H₅ | H | |
| 173 | benzoyl | H | n-C₃H₇ | C₂H₅ | H | |
| 174 | benzoyl | H | C₂H₅ | C₂H₅ | H | |
| 175 | benzoyl | H | C₂H₅ | CH₂—CH=CH₂ | H | |
| 176 | benzoyl | H | n-C₃H₇ | CH₂—CH=CH₂ | H | |

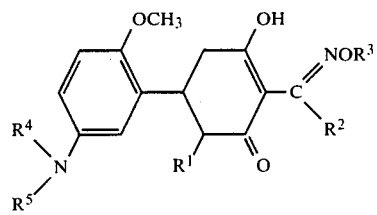

| | | | | | | |
|---|---|---|---|---|---|---|
| 92 | H | H | CH₃ | C₂H₅ | H | oil |
| 93 | H | H | C₂H₅ | C₂H₅ | H | |
| 94 | H | H | n-C₃H₇ | C₂H₅ | H | |
| 95 | acetyl | H | CH₃ | C₂H₅ | H | 152–153 |
| 96 | acetyl | H | C₂H₅ | C₂H₅ | H | 133–135 |
| 97 | acetyl | H | n-C₃H₇ | C₂H₅ | H | 138–140 |
| 98 | methoxycarbonyl | H | CH₃ | C₂H₅ | H | 129–133 |
| 99 | methoxycarbonyl | H | n-C₃H₇ | C₂H₅ | H | 106–108 |
| 100 | methoxycarbonyl | H | n-C₃H₇ | CH₂—CH=CH₂ | H | |
| 101 | methylthiocarbonyl | H | CH₃ | C₂H₅ | H | 134–136 |
| 102 | methylthiocarbonyl | H | n-C₃H₇ | C₂H₅ | H | |
| 177 | 3-methoxypropionyl | H | n-C₃H₇ | C₂H₅ | H | (NMR data) |
| 178 | 3-methoxypropionyl | H | C₂H₅ | C₂H₅ | H | |
| 179 | benzoyl | H | C₂H₅ | C₂H₅ | H | 179–180 |
| 180 | benzoyl | H | n-C₃H₇ | C₂H₅ | H | 134–136 |
| 103 | N—methylcarbamoyl | H | CH₃ | C₂H₅ | H | 167–169 |
| 104 | N—methylcarbamoyl | H | C₂H₅ | C₂H₅ | H | 156–158 |
| 105 | N—methylcarbamoyl | H | n-C₃H₇ | C₂H₅ | H | 180–181 |
| 106 | N—methoxy—N—methylcarbamoyl | H | CH₃ | C₂H₅ | H | 118–120 |
| 107 | N—methoxy—N—methylcarbamoyl | H | n-C₃H₇ | C₂H₅ | H | 84–87 |

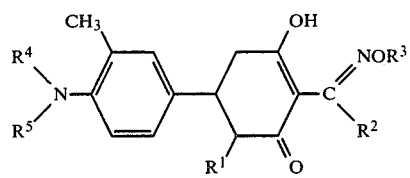

| | | | | | | |
|---|---|---|---|---|---|---|
| 108 | H | H | n-C₃H₇ | C₂H₅ | H | (NMR data) |
| 109 | acetyl | H | n-C₃H₇ | C₂H₅ | H | 119 |
| 110 | acetyl | H | n-C₃H₇ | CH₂—CH=CH₂ | H | |
| 111 | N—methylcarbamoyl | H | n-C₃H₇ | C₂H₅ | H | 152–153 |
| 112 | N—methylcarbamoyl | H | n-C₃H₇ | CH₂—CH=CH₂ | H | |
| 181 | N—methylcarbamoyl | H | C₂H₅ | CH₂—CH=CH₂ | H | |
| 182 | N—methylcarbamoyl | H | C₂H₅ | C₂H₅ | H | 139–142 |
| 183 | N—methoxy—N—methylcarbamoyl | H | C₂H₅ | C₂H₅ | H | 120–123 |
| 184 | N—methoxy—N—methylcarbamoyl | H | n-C₃H₇ | C₂H₅ | H | |
| 185 | methylthiocarbonyl | H | C₂H₅ | C₂H₅ | H | 130–132 |
| 186 | methylthiocarbonyl | H | n-C₃H₇ | C₂H₅ | H | |
| 187 | methoxycarbonyl | H | n-C₃H₇ | C₂H₅ | H | 105–109 |
| 188 | methoxycarbonyl | H | n-C₃H₇ | CH₂—CH=CH₂ | H | |
| 189 | methoxycarbonyl | H | C₂H₅ | CH₂—CH=CH₂ | H | |
| 190 | methoxycarbonyl | H | C₂H₅ | C₂H₅ | H | 131–134 |
| 191 | chloroacetyl | H | C₂H₅ | C₂H₅ | H | 128–129 |
| 192 | chloroacetyl | H | C₂H₅ | CH₂—CH=CH₂ | H | |
| 193 | chloroacetyl | H | n-C₃H₇ | CH₂—CH=CH₂ | H | |
| 194 | chloroacetyl | H | n-C₃H₇ | C₂H₅ | H | |
| 195 | methoxyacetyl | H | n-C₃H₇ | C₂H₅ | H | (NMR data) |
| 196 | methoxyacetyl | H | n-C₃H₇ | CH₂—CH=CH₂ | H | |
| 197 | methoxyacetyl | H | C₂H₅ | CH₂—CH=CH₂ | H | |
| 198 | methoxyacetyl | H | C₂H₅ | C₂H₅ | H | 158–160 |
| 199 | acetoxyacetyl | H | C₂H₅ | C₂H₅ | H | 123–125 |
| 200 | acetoxyacetyl | H | C₂H₅ | CH₂—CH=CH₂ | H | |
| 201 | acetoxyacetyl | H | C₂H₅ | CH₂CH₂Cl | H | |
| 202 | acetoxyacetyl | H | C₂H₅ | (E)-CH₂—CH=CH—CH₃ | H | |
| 203 | acetoxyacetyl | H | C₂H₅ | (E)-CH₂—CH=CH—Cl | | |
| 204 | acetoxyacetyl | H | n-C₃H₇ | C₂H₅ | H | |
| 205 | acetoxyacetyl | H | n-C₃H₇ | CH₂—CH=CH₂ | H | |
| 206 | acetoxyacetyl | H | n-C₃H₇ | CH₂—CH₂Cl | H | |

| | | | | | | |
|---|---|---|---|---|---|---|
| 207 | acetoxyacetyl | H | n-C₃H₇ | (E)-CH₂CH=CH—CH₃ | H | |
| 208 | acetoxyacetyl | H | n-C₃H₇ | (E)-CH₂—CH=CH—Cl | H | |
| 209 | propioxyacetyl | H | n-C₃H₇ | C₂H₅ | H | |
| 210 | propioxyacetyl | H | C₂H₅ | C₂H₅ | H | |
| 211 | benzoyloxyacetyl | H | C₂H₅ | C₂H₅ | H | |
| 212 | benzoyloxyacetyl | H | n-C₃H₇ | C₂H₅ | H | |
| 213 | benzoyl | H | n-C₃H₇ | C₂H₅ | H | 145–148 |
| 214 | benzoyl | H | C₂H₅ | C₂H₅ | H | 123–126 |
| 215 | methylsulfonyl | H | C₂H₅ | C₂H₅ | H | 126–130 |
| 216 | methylaminosulfonyl | H | C₂H₅ | C₂H₅ | H | 145–148 |
| 217 | acetyl | H | C₂H₅ | C₂H₅ | H | 153–156 |

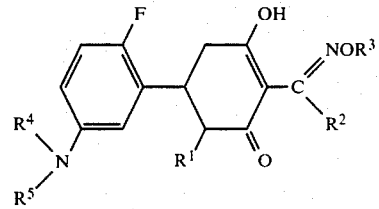

| | | | | | | |
|---|---|---|---|---|---|---|
| 113 | H | H | n-C₃H₇ | C₂H₅ | H | (NMR data) |
| 114 | acetyl | H | n-C₃H₇ | C₂H₅ | H | 120–122 |
| 115 | benzoyl | H | n-C₃H₇ | C₂H₅ | H | 116–117 |
| 116 | N—methylcarbamoyl | H | n-C₃H₇ | C₂H₅ | H | 120–122 |

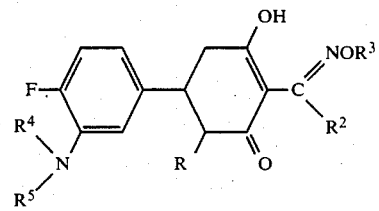

| | | | | | | |
|---|---|---|---|---|---|---|
| 117 | acetyl | H | n-C₃H₇ | C₂H₅ | H | 120–122 |
| 118 | methylsulfonyl | H | n-C₃H₇ | C₂H₅ | H | |
| 119 | chloromethylsulfonyl | H | n-C₃H₇ | C₂H₅ | H | |
| 120 | trifluoromethylsulfonyl | H | n-C₃H₇ | C₂H₅ | H | |
| 218 | H | H | n-C₃H₇ | C₂H₅ | H | (NMR data) |
| 219 | chloroacetyl | H | n-C₃H₇ | C₂H₅ | H | 111–115 |
| 220 | chloroacetyl | H | n-C₃H₇ | CH₂—CH=CH₂ | H | |
| 221 | chloroacetyl | H | C₂H₅ | CH₂—CH=CH₂ | H | |
| 222 | chloroacetyl | H | C₂H₅ | C₂H₅ | H | |
| 223 | acetyl | H | C₂H₅ | C₂H₅ | H | |
| 224 | acetyl | H | n-C₃H₇ | CH₂—CH=CH₂ | H | 109–111 |
| 225 | acetyl | H | C₂H₅ | CH₂CH₂Cl | H | |
| 226 | acetyl | H | n-C₃H₇ | (E)-CH₂—CH=CH—CH₃ | H | 121–123 |
| 227 | acetyl | H | C₂H₅ | (E)-CH₂—CH=CH—Cl | H | |
| 228 | methoxyacetyl | H | n-C₃H₇ | C₂H₅ | H | 94–96 |
| 229 | methoxyacetyl | H | n-C₃H₇ | CH₂—CH=CH₂ | H | |
| 230 | methoxyacetyl | H | C₂H₅ | C₂H₅ | H | |
| 231 | methoxyacetyl | H | C₂H₅ | CH₂—CH=CH₂ | H | |
| 232 | acetyl | H | n-C₃H₇ | (E)-CH₂—CH=CH—Cl | H | 128–130 |
| 233 | benzoyl | H | C₂H₅ | C₂H₅ | H | |
| 234 | benzoyl | H | C₂H₅ | CH₂—CH=CH₂ | H | |
| 235 | benzoyl | H | n-C₃H₇ | CH₂—CH=CH₂ | H | |
| 236 | benzoyl | H | n-C₃H₇ | C₂H₅ | H | 125–128 |
| 237 | 3-methoxypropionyl | H | n-C₃H₇ | C₂H₅ | H | 112–114 |
| 238 | 3-methoxypropionyl | H | C₂H₅ | C₂H₅ | H | |
| 239 | methoxycarbonyl | H | C₂H₅ | C₂H₅ | H | |
| 240 | methoxycarbonyl | H | n-C₃H₇ | C₂H₅ | H | (NMR data) |
| 241 | methylthiocarbonyl | H | n-C₃H₇ | C₂H₅ | H | 94–97 |
| 242 | methylthiocarbonyl | H | C₂H₅ | C₂H₅ | H | |
| 243 | N—methylcarbamoyl | H | n-C₃H₇ | C₂H₅ | H | |
| 244 | N—methylcarbamoyl | H | C₂H₅ | C₂H₅ | H | 117–121 |
| 245 | N—methoxy—N—methylcarbamoyl | H | n-C₃H₇ | C₂H₅ | H | 83–86 |
| 246 | N—methoxy—N—methylcarbamoyl | H | C₂H₅ | C₂H₅ | H | |
| 247 | methylsulfonyl | H | C₂H₅ | C₂H₅ | H | |
| 248 | methylsulfonyl | H | n-C₃H₇ | C₂H₅ | H | |
| 249 | methylaminosulfonyl | H | n-C₃H₇ | C₂H₅ | H | (NMR data) |
| 250 | methylaminosulfonyl | H | C₂H₅ | C₂H₅ | H | |
| 251 | propionyl | H | n-C₃H₇ | C₂H₅ | H | |
| 252 | propionyl | H | C₂H₅ | C₂H₅ | H | |
| 253 | butyryl | H | n-C₃H₇ | C₂H₅ | H | |
| 254 | butyryl | H | C₂H₅ | C₂H₅ | H | |
| 255 | cyclohexylcarbonyl | H | n-C₃H₇ | C₂H₅ | H | |
| 256 | cyclohexylcarbonyl | H | C₂H₅ | C₂H₅ | H | |
| 257 | N,N—dimethylcarbamoyl | H | n-C₃H₇ | C₂H₅ | H | |

-continued

| | | | | | | |
|---|---|---|---|---|---|---|
| 258 | N,N—dimethylcarbamoyl | H | n-C$_3$H$_7$ | C$_2$H$_5$ | H | |
| 259 | ethoxycarbonyl | H | n-C$_3$H$_7$ | C$_2$H$_5$ | H | |
| 260 | ethoxycarbonyl | H | C$_2$H$_5$ | C$_2$H$_5$ | H | |

| Compound no. | R$^6$ | R$^5$ | R$^1$ | R$^2$ | R$^3$ | R$^4$ | M.p. [°C.] |
|---|---|---|---|---|---|---|---|

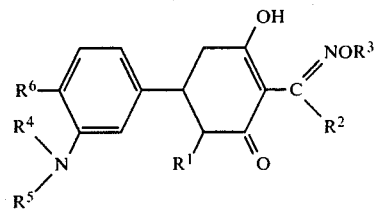

| 121 | chlorine | acetyl | H | n-C$_3$H$_7$ | C$_2$H$_5$ | H | 136–139 |
| 122 | hydroxy | acetyl | H | n-C$_3$H$_7$ | C$_2$H$_5$ | H | 125–126 |
| 123 | tert.-butoxy | acetyl | H | n-C$_3$H$_7$ | C$_2$H$_5$ | H | |
| 124 | allyloxy | acetyl | H | n-C$_3$H$_7$ | C$_2$H$_5$ | H | |
| 125 | propargyloxy | acetyl | H | n-C$_3$H$_7$ | C$_2$H$_5$ | H | |
| 261 | hydroxy | H | H | C$_2$H$_5$ | C$_2$H$_5$ | H | |
| 262 | hydroxy | acetyl | H | C$_2$H$_5$ | C$_2$H$_5$ | H | 144–146 |
| 263 | hydroxy | chloroacetyl | H | n-C$_3$H$_7$ | C$_2$H$_5$ | H | 170–172 |
| 264 | hydroxy | benzoyl | H | n-C$_3$H$_7$ | C$_2$H$_5$ | H | 150–152 |
| 265 | hydroxy | benzoyl | H | C$_2$H$_5$ | C$_2$H$_5$ | H | 122–126 |
| 266 | hydroxy | N—methylcarbamoyl | H | n-C$_3$H$_7$ | C$_2$H$_5$ | H | 108–110 |
| 267 | chlorine | H | H | n-C$_3$H$_7$ | C$_2$H$_5$ | H | 138 (decomp.) |
| 268 | chlorine | acetyl | H | n-C$_3$H$_7$ | (E)-CH$_2$—CH=CH—Cl | H | 78–80 |
| 269 | chlorine | benzoyl | H | n-C$_3$H$_7$ | C$_2$H$_5$ | H | 124–127 |
| 270 | chlorine | methoxyacetyl | H | n-C$_3$H$_7$ | C$_2$H$_5$ | H | 98–103 |
| 271 | chlorine | chloroacetyl | H | n-C$_3$H$_7$ | C$_2$H$_5$ | H | 96–101 |
| 130 | ethylthio | acetyl | H | n-C$_3$H$_7$ | C$_2$H$_5$ | H | |
| 131 | ethylthio | benzoyl | H | n-C$_3$H$_7$ | C$_2$H$_5$ | H | |
| 132 | ethylsulfynyl | acetyl | H | n-C$_3$H$_7$ | C$_2$H$_5$ | H | |
| 133 | ethylsulfynyl | benzoyl | H | n-C$_3$H$_7$ | C$_2$H$_5$ | H | |
| 134 | ethylsulfynyl | acetyl | H | n-C$_3$H$_7$ | C$_2$H$_5$ | H | |
| 135 | ethylsulfynyl | benzoyl | H | n-C$_3$H$_7$ | C$_2$H$_5$ | H | |

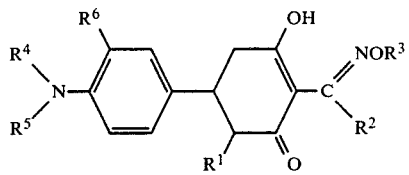

| 126 | nitro | acetyl | H | n-C$_3$H$_7$ | C$_2$H$_5$ | H | 118–120 |
| 127 | nitro | acetyl | H | n-C$_3$H$_7$ | CH$_2$—CH=CH$_2$ | H | |
| 128 | amino | acetyl | H | n-C$_3$H$_7$ | C$_2$H$_5$ | H | |
| 129 | amino | acetyl | H | n-C$_3$H$_7$ | CH$_2$—CH=CH$_2$ | H | |
| 272 | nitro | benzoyl | H | n-C$_3$H$_7$ | C$_2$H$_5$ | H | |
| 273 | nitro | benzoyl | H | n-C$_3$H$_7$ | C$_2$H$_5$ | H | |
| 274 | amino | benzoyl | H | n-C$_3$H$_7$ | C$_2$H$_5$ | H | |
| 275 | amino | benzoyl | H | n-C$_3$H$_7$ | CH$_2$—CH=CH$_2$ | H | |
| 276 | chlorine | benzoyl | H | n-C$_3$H$_7$ | C$_2$H$_5$ | H | |
| 277 | chlorine | benzoyl | H | n-C$_3$H$_7$ | CH$_2$—CH=CH$_2$ | H | |
| 278 | chlorine | acetyl | H | n-C$_3$H$_7$ | C$_2$H$_5$ | H | |
| 279 | chlorine | acetyl | H | n-C$_3$H$_7$ | CH$_2$CH=CH$_2$ | H | |
| 280 | bromine | acetyl | H | n-C$_3$H$_7$ | C$_2$H$_5$ | H | |
| 281 | bromine | acetyl | H | n-C$_3$H$_7$ | CH$_2$—CH=CH$_2$ | H | |
| 282 | bromine | benzoyl | H | n-C$_3$H$_7$ | C$_2$H$_5$ | H | |
| 283 | bromine | benzoyl | H | n-C$_3$H$_7$ | CH$_2$—CH=CH$_2$ | H | |
| 284 | fluorine | benzoyl | H | C$_2$H$_5$ | C$_2$H$_5$ | H | 151–153 |
| 285 | fluorine | benzoyl | H | C$_2$H$_5$ | C$_2$H$_5$ | H | |
| 286 | fluorine | benzoyl | H | C$_2$H$_5$ | CH$_2$—CH=CH$_2$ | | |
| 287 | fluorine | benzoyl | H | C$_2$H$_5$ | (E)-CH$_2$—CH=CH—Cl | H | 156–157 |
| 288 | fluorine | benzoyl | H | C$_2$H$_5$ | (E)-CH$_2$—CH=CH—CH$_3$ | H | |
| 289 | fluorine | benzoyl | H | n-C$_3$H$_7$ | C$_2$H$_5$ | H | 163–165 |
| 290 | fluorine | benzoyl | H | n-C$_3$H$_7$ | CH$_2$CH$_2$Cl | H | |
| 291 | fluorine | benzoyl | H | n-C$_3$H$_7$ | CH$_2$—CH=CH$_2$ | H | 121–123 |
| 292 | fluorine | benzoyl | H | n-C$_3$H$_7$ | (E)-CH$_2$—CH=CH—Cl | H | 108–112 |
| 293 | fluorine | benzoyl | H | n-C$_3$H$_7$ | (E)-CH$_2$—CH=CH—CH$_3$ | H | |
| 294 | fluorine | o-toluyl | H | n-C$_3$H$_7$ | C$_2$H$_5$ | H | |
| 295 | fluorine | o-toluyl | H | n-C$_3$H$_7$ | CH$_2$—CH=CH$_2$ | H | |
| 296 | fluorine | o-toluyl | H | C$_2$H$_5$ | C$_2$H$_5$ | H | |
| 297 | fluorine | o-toluyl | H | C$_2$H$_5$ | CH$_2$—CH=CH$_2$ | H | |
| 298 | fluorine | acetyl | H | C$_2$H$_5$ | C$_2$H$_5$ | H | |
| 299 | fluorine | acetyl | H | C$_2$H$_5$ | CH$_2$—CH=CH$_2$ | H | |

| | | | | | | |
|---|---|---|---|---|---|---|
| 300 | fluorine | acetyl | H | n-C$_3$H$_7$ | C$_2$H$_5$ | H |
| 301 | fluorine | acetyl | H | n-C$_3$H$_7$ | CH$_2$—CH=CH$_2$ | H |
| 302 | fluorine | H | H | n-C$_3$H$_7$ | C$_2$H$_5$ | H oil |

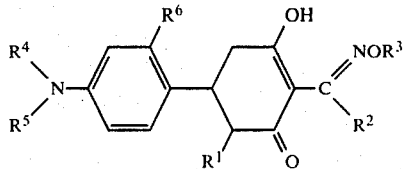

| | | | | | | |
|---|---|---|---|---|---|---|
| 303 | fluorine | benzoyl | H | C$_2$H$_5$ | C$_2$H$_5$ | H |
| 304 | fluorine | benzoyl | H | C$_2$H$_5$ | CH$_2$CH$_2$Cl | H |
| 305 | fluorine | benzoyl | H | C$_2$H$_5$ | CH$_2$—CH=CH$_2$ | H |
| 306 | fluorine | benzoyl | H | C$_2$H$_5$ | (E)-CH$_2$—CH=CH—Cl | H |
| 307 | fluorine | benzoyl | H | C$_2$H$_5$ | (E)-CH$_2$—CH=CH—CH$_3$ | H |
| 308 | fluorine | benzoyl | H | n-C$_3$H$_7$ | C$_2$H$_5$ | H (NMR data) |
| 309 | fluorine | benzoyl | H | n-C$_3$H$_7$ | CH$_2$CH$_2$Cl | H |
| 310 | fluorine | benzoyl | H | n-C$_3$H$_7$ | CH$_2$—CH=CH$_2$ | H |
| 311 | fluorine | benzoyl | H | n-C$_3$H$_7$ | (E)-CH$_2$—CH=CH—Cl | H |
| 312 | fluorine | benzoyl | H | n-C$_3$H$_7$ | (E)-CH$_2$—CH=CH—CH$_3$ | H |
| 313 | chlorine | benzoyl | H | C$_2$H$_5$ | C$_2$H$_5$ | H |
| 314 | chlorine | benzoyl | H | C$_2$H$_5$ | CH$_2$—CH=CH$_2$ | H |
| 315 | chlorine | benzoyl | H | n-C$_3$H$_7$ | C$_2$H$_5$ | H |
| 316 | chlorine | benzoyl | H | n-C$_3$H$_7$ | CH$_2$—CH=CH$_2$ | H |

The cyclohexenone derivatives of the formula I may be identified by characteristic $^1$H-NMR spectroscopic data (chemical shift in δ values (ppm) in CDCl$_3$, based on tetramethylsilane as internal standard; s=singlet, d=doublet, q=quartet, m=multiplet):

| Compound no. | Characteristic signals |
|---|---|
| 76 | 1.0 (t, 3H); 3.9 (s, 3H); 4.0–4.4 (m, 6H) |
| 77 | 1.0 (t, 3H); 3.85 (s, 3H); 4.0–4.3 (m, 6H) |
| 91 | 2.2 (s, 3H); 2.45 (s, 3H); 3.75 (s, 3H); 6.95 (d, 1H); 7.15 (t, 1H); 8.20 (d, 1H) |
| 95 | 2.2 (s, 3H); 2.4 (s, 3H); 3.8 (s, 3H); 6.8 (d, 1H); 7.45 (d, 1H) |
| 108 | 0.95 (t, 3H); 4.1 (q, 2H); 6.55 (d, 1H); 6.75 (s, 1H); 7.10 (d, 1H) |
| 113 | 1.3 (t, 3H); 6.4–6.6 (m), 6.85 (t) |
| 136 | 3.6 (s); 3.8 (s); 6.5–6.8 (m) |
| 177 | 2.95 (t); 6.8 (d); 7.25 (m); 7.45 (m), 8.35 (s) |
| 195 | 2.15 (s); 3.4 (s); 8.1 (s); 6.9–7.1 (m); 7.85 (d) |
| 218 | 0.95 (t); 1.3 (t); 4.05–4.2 (q) |
| 240 | 2.95 (t); 3.35 (m);, 3.8 (s); 4.15 (q) |
| 249 | 0.95 (t); 4.1 (q); 4.75 (q); 6.7 (s); 7.4 (d) |
| 308 | 2.97 (t); 4.12 (q); 7.86 (d). |

The cyclohexenone derivatives of the formula I, and their salts, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, haptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 7 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 109 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 111 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 7 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 33 is intimately mixed with 97 parts by weight of particulate kaolin. A dust is obtained containing 3% by weight of the active ingredient.

VII. 30 parts by weight of compound no. 56 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 111 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

IX. 10 parts of compound no. 289 is mixed with 90 parts by weight of a mixture of 93 parts by weight of xylene and 7 parts by weight of the adduct of 8 moles of ethylene oxide and 1 mole of nonyl phenol. A solution is obtained which contains 10 wt% of active ingredient.

The active ingredients, or agents containing them, may be applied pre- or postemergence. If certain crop plants tolerate the active ingredients less well on postemergence treatment, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combatted and their growth stage, and varies from 0.025 to 3 kg/ha, but is preferably from 0.06 to 0.5 kg/ha.

The action of the cyclohexenone derivatives of the formula I on plant growth is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were 0.06 to 0.5 kg of active ingredient per hectare. No covers were placed on the vessels in this method.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Alopecurus myosuroides, Avena fatua, Avena sativa, Echinochloa crus-* galli, Glycine max., Lolium multiflorum, Oryza sativa, Setaria italica, Sinapis alba, and Sorghum halepense.

On preemergence application, for example compounds nos. 1, 7, 33 and 56 proved to be herbicidally effective on plants from the grasses family, whereas Sinapis alba, as a dicotyledonous representative, remained completely undamaged.

On postemergence application, for instance compounds nos. 56 and 114 at 0.5 kg/ha, and nos. 109 and 111 at 0.06 kg/ha had a strong herbicidal action on grasses selected by way of example, whereas soybeans, as dicotyledonous crop plants, were not damaged. Compound no. 7 is, for example, suitable for combatting Echinochloa crus-galli in rice.

Unwanted grasses can be controlled with small amounts of, for instance, compounds nos. 109 and 111; soybeans as dicotyledonous crop plants, remained undamaged.

Compounds nos. 60, 64 and 75 selected by way of example combatted unwanted grassy plants well, and were tolerated well by soybeans.

Compound no. 103, for instance, had a high level of action on plants from the Gramineae family and caused no damage to wheat.

Unwanted grassy plants can be combatted well with compounds nos. 117, 126 and 127 selected by way of example. Alfalfa as crop plant suffered no damage.

For example compound no. 289 is suitable for controlling important grassy weeds in rice. Only slight damage was caused to the crop plant.

In view of the spectrum of weeds which can be combatted, the tolerance of the active ingredients according to the invention by crop plants, the desired influence on the growth of crop plants, and in view of the numerous application methods possible, the cyclohexenone derivatives of the formula I may be used in a large number of crop plants.

The following may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum | cotton |

-continued

| Botanical name | Common name |
| --- | --- |
| Gossypium vitifolium) | |
| Helianthus annuus | sunflowers |
| Helianthus tuberosus | Jerusalem artichoke |
| Hevea brasiliensis | rubber plants |
| Hardeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the cyclohexenone derivatives of the formula I, and their salts, may be mixed and applied together with numerous representatives of other hericidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acid derivatives, etc.

It may also be useful to apply the compounds of the formula I, either alone or in combination with other herbicides, in admixture with other crop protection agents, e.g., agents for combatting pests or phytopathogenic fungi or bacteria. The compounds may also be mixed with solutions of mineral salts used to remedy

We claim:
1. A cyclohexenone of the formula

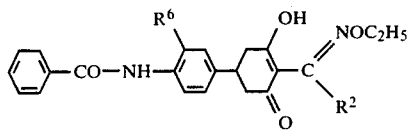

wherein $R^6$ is a member selected from the group consisting of chlorine, bromine and fluorine and $R^2$ is a member selected from the group consisting of ethyl and n-propyl.

2. The composition of claim 1 wherein $R^6$ is fluorine and $R^2$ is member selected from the group consisting of ethyl and n-propyl.

3. A cyclohexenone of the formula

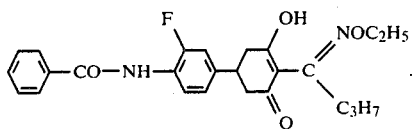

* * * * *